United States Patent [19]
Garrett

[11] Patent Number: 6,129,892
[45] Date of Patent: Oct. 10, 2000

[54] METHOD AND APPLICATION UNIT FOR ELIMINATING HUMAN URINE ODOR

[76] Inventor: John W. Garrett, 9403 Alameda Ave., Richmond, Va. 23294

[21] Appl. No.: 09/113,320

[22] Filed: Jul. 10, 1998

[51] Int. Cl.[7] .............................. A61L 9/00; A61L 11/00
[52] U.S. Cl. ...................... 422/5; 43/1; 422/1; 424/76.5; 424/76.6
[58] Field of Search .............................. 422/1, 4, 5; 43/1, 43/900; 424/400, 489, 76.1, 76.5, 76.6

[56] References Cited

U.S. PATENT DOCUMENTS

| | | | |
|---|---|---|---|
| 2,778,774 | 1/1957 | Buslik | 422/5 |
| 3,884,804 | 5/1975 | Robinson et al. | 422/5 |
| 4,108,771 | 8/1978 | Weiss | 422/5 |
| 4,256,728 | 3/1981 | Nishino et al. | 422/122 |
| 4,909,986 | 3/1990 | Kobayashi et al. | 422/4 |
| 5,039,481 | 8/1991 | Pacifici et al. | 422/4 |
| 5,585,107 | 12/1996 | Vickers | 424/402 |
| 5,891,391 | 4/1999 | Fore | 422/5 |
| 5,894,608 | 4/1999 | Birbara | 4/144.3 |

*Primary Examiner*—Krisanne Thornton
*Attorney, Agent, or Firm*—Lawrence Douglas Bush

[57] ABSTRACT

The present invention consists of a method for storing an acidified, charcoal slurry and applying it to remove ammonia and absorb other odor-causing chemicals from human urine. Packaged in a plastic, squeeze bottle, the slurry can be carried in a pocket and used by hunters and outdoorsmen to eliminate urine odors that would otherwise alert wildlife of their presence. The present invention represents a novel way of storing and transporting the slurry for ready use, as well as a unique way to dispense the slurry for chemical reaction with the human urine.

17 Claims, 4 Drawing Sheets

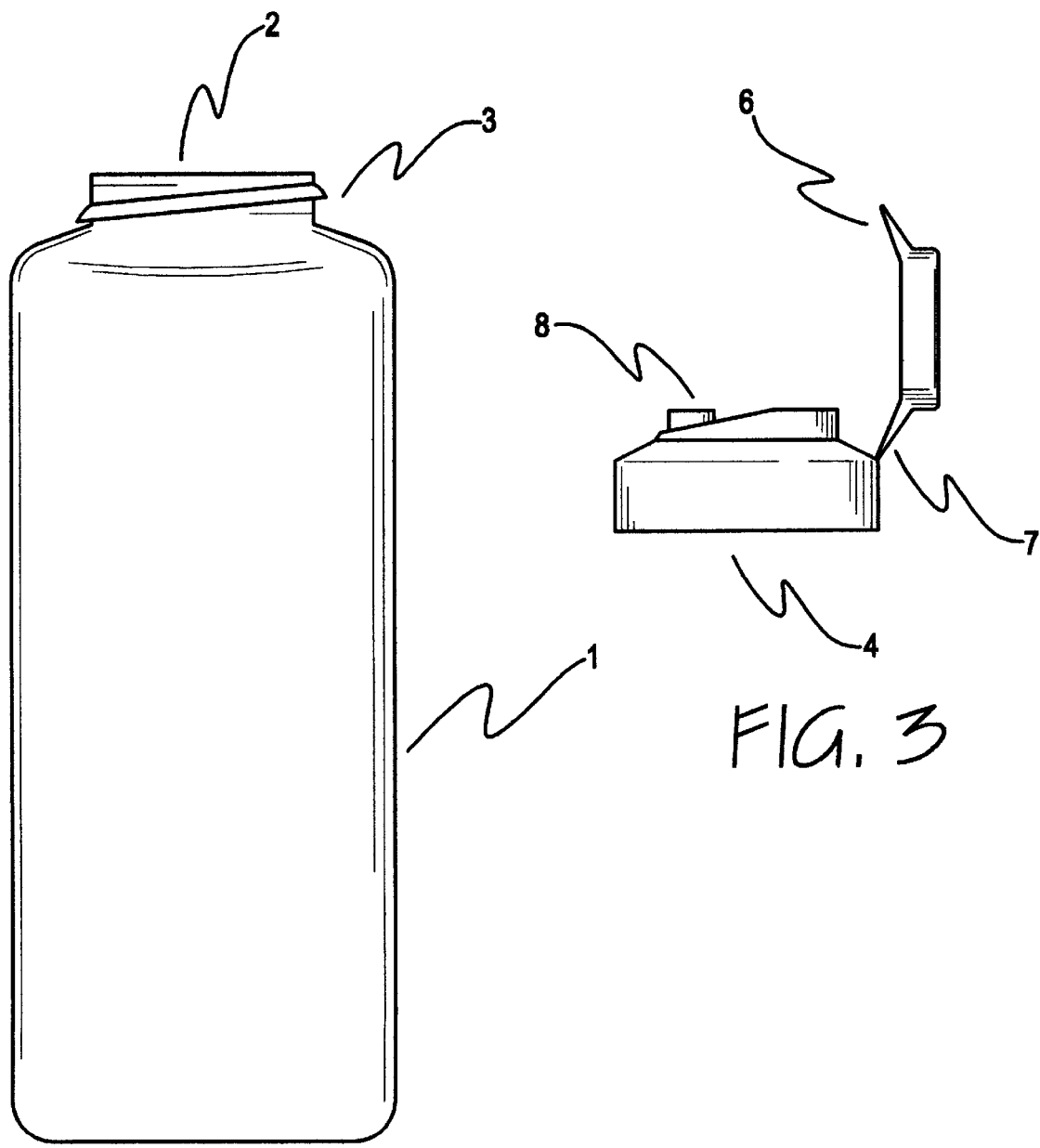

METHOD AND APPLICATION UNIT FOR ELIMINATING HUMAN URINE ODOR

The subject of the present invention is the reduction of odors associated with urine by applying a mixture of acid and activated charcoal, which are packaged in an applicator for convenient storage and easy use. More specifically, the present invention is intended as an aid for hunters by reducing the odors from their urine to levels that will not alarm and thereby repel game animals.

BACKGROUND OF THE INVENTION

Large game animals, such as deer, bear and elk, have a well-developed sense of smell. They use the sense of smell to detect possible danger, which they associate with unfamiliar or unusual odors. These animals will avoid entering an area if they preceive danger from an odor, such as human urine.

Hunters and naturalists who need to urinate while in the outdoors have to be concerned that the scent or odor from their urine will alert wildlife of their presence. One approach to this problem is to carry a container, such as a jar or bottle, that will hold the urine. The container has to be sealed after use and carried around for the rest of the time the person is outdoors. Another approach is to dig a deep hole into which the person can urinate and then fill and cover the hole with dirt. Both approaches pose obvious problems that are overcome by the present invention.

The present invention takes a mixture of activated charcoal and an acid, such as citric acid, and places them in a small, pocket-sized, squeeze bottle for easy carrying and use. Before urinating, the user makes an indentation in the ground and pours a small amount of the mixture into the indentation. The user then urinates on the same ground that has been wetted with the mixture. After urinating, the user saturates the ground area containing urine with the mixture. Usually, only three to four ounces of the mixture are needed. The effect of the mixture is to eliminate essentially all of the ammonia and other odors given off by the urine.

The effectiveness of acid in neutralizing ammonia is well known. It is also well known that activated charcoal is useful in absorbing chemicals and odors. Both acid and activated charcoal have been employed over the years in a variety of ways to control and eliminate odors from sewage and septic systems. However, the present invention represents a new and novel method for applying these chemicals, as well as a useful application unit for storing and dispensing these chemicals.

SUMMARY OF THE PRESENT INVENTION

The present invention is essentially an acidified activated charcoal slurry. It reduces the odors from urine by two distinct chemical mechanisms.

First, dissolved ammonia in the urine is chemically removed by converting it into a non-volatile form. This conversion is accomplished through an acid-base reaction:

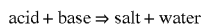

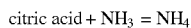

The ammonia acts as a base and is neutralized by the citric acid to form ammonium citrate salts and water. The ammonium citrate is non-volatile, and hence, scent free.

Second, ammonia and other odor-causing components in urine are reduced by physical absorption onto activated carbon. The carbon acts as a "chemical sponge" for odor-causing compounds. Once the scented compounds have been absorbed onto the carbon, their volatility is greatly reduced, which helps to eliminate their scent.

The present invention incorporates the chemical properties of the acidified charcoal slurry into a convenient and easy to apply container. A further advantage of the mixture is that the ingredients are environmentally safe. The container incorporated with the mixture in the present invention is a squeeze bottle with a nozzle opening and a cap. The squeeze bottle is hand-sized and can be carried in a garment pocket or attached to a belt; this gives the invention the advantage of being very portable. Since the bottle is hand-sized, it can be easily gripped and squeezed when applying the mixture; these features give the present invention the advantages of convenience and easy use.

The bottle is an efficient applicator for the mixture, because the amount of mixture needed for one use can be dispensed and the applicator can be closed. The applicator or bottle holds enough mixture for several uses. Once the applicator is empty, it can be refilled with the mixture and reused many times. In addition, the present invention has the feature of being readily disposable, by virtue of its small size and the common nature of the ingredients for the mixture.

This foregoing list of advantages is not intended to be all inclusive, inasmuch as other advantages are discussed elsewhere herein and additional advantages may be apparent concerning the usefulness of the method and applicator relative to controlling odors produced from urine.

DETAILED DRAWINGS

FIG. 2 is a side view of the uncapped squeeze bottle.

FIG. 3 is a side view of the cap in the open position.

PREFERRED EMBODIMENT FOR THE PRESENT INVENTION

The preferred mixture for the present invention is one part of activated charcoal to 11 parts of citric acid solution, having a pH of approximately 2.2. For a 12-ounce container, the preferred mixture is achieved using: 1.0 fluid ounce of activated charcoal, 0.5 fluid ounce of dry citric acid, and 10.5 fluid ounces of water. The pH level of the preferred mixture is approximately 2.7. It should be noted that different mixture ratios can be used with good results, and different kinds of acid with higher or lower pH levels can also work effectively.

The advantages of the preferred mixture are (1) the low amount of activated charcoal, which allows for better mixing and easier spreading and (2) the acid concentration is relatively high, which means that less of the mixture has to be used so that one bottle holds enough mixture for several applications.

The acid used in the preferred mixture is an anhydrous, food grade, citric acid; it is made by Jungbunzlauer of Austria and is identified as C6H807. The activated charcoal in the preferred mixture is a powdered, activated carbon product made by Royal Oak Enterprises, Inc.; it is identified as Acticarb or Water Carb.

Figure 1:
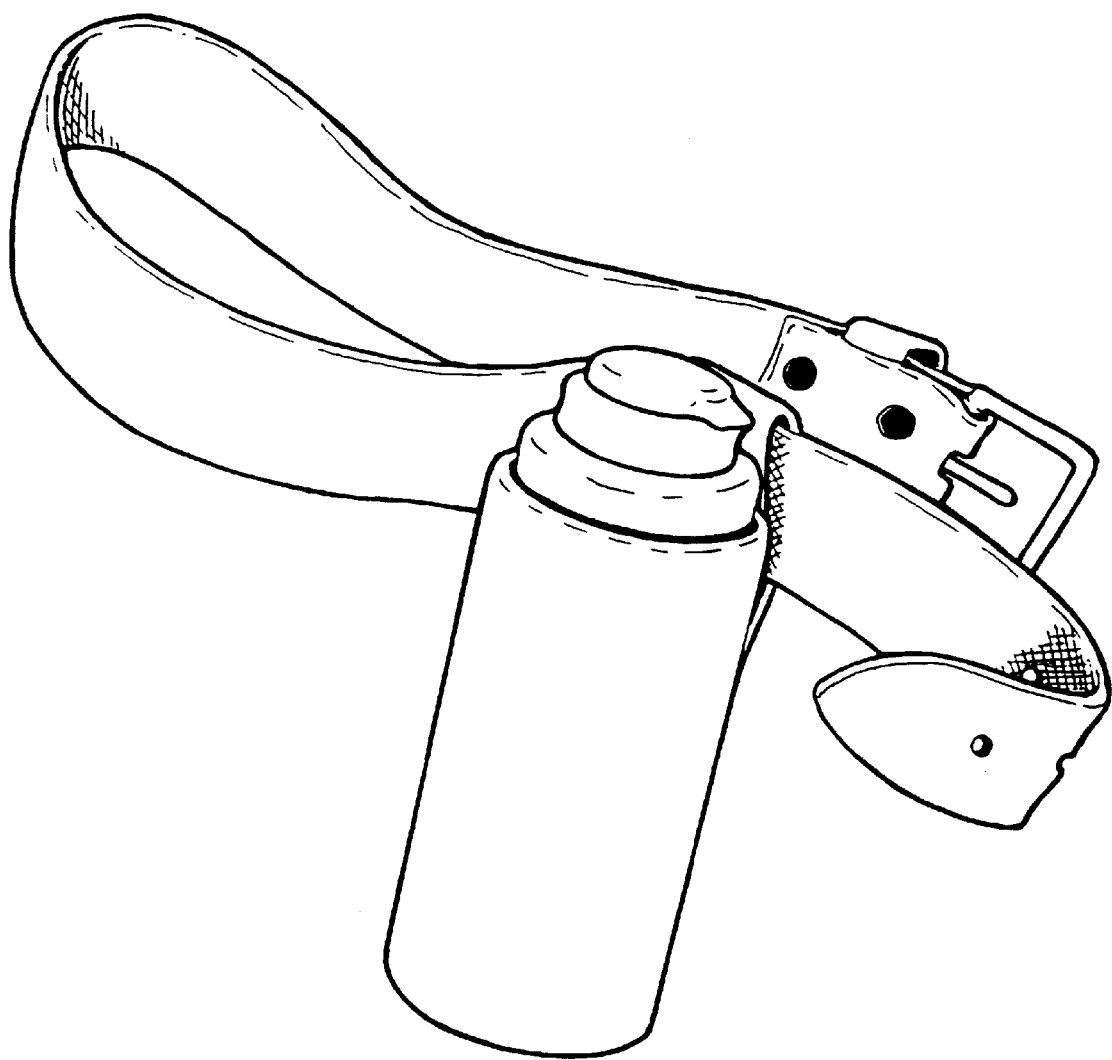
FIG. 1 shows a perspective view of the squeeze bottle for the present invention, as attached to a belt.
Figure 4:
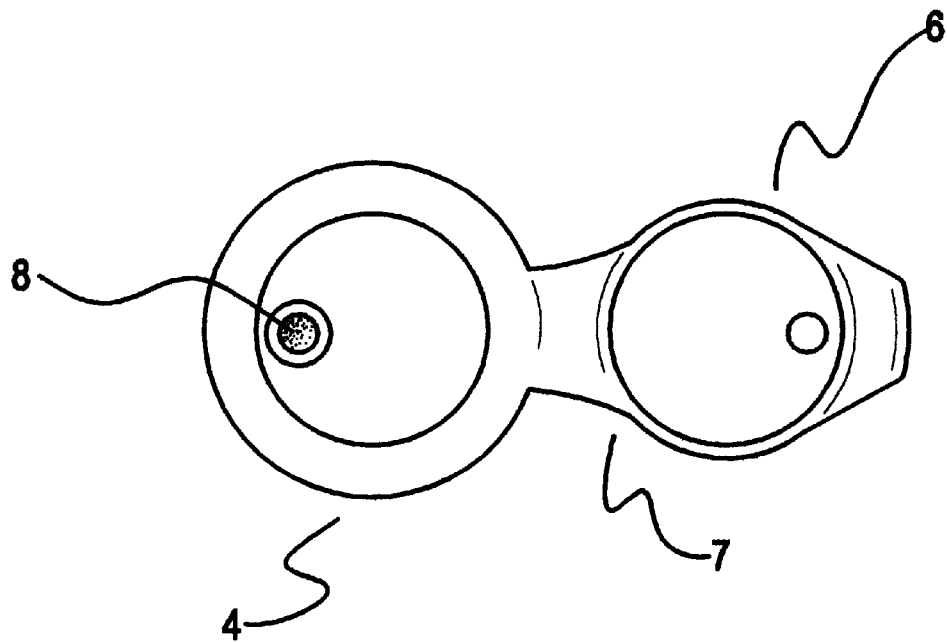
FIG. 4 is a top view of the cap in the open position.
Figure 5:
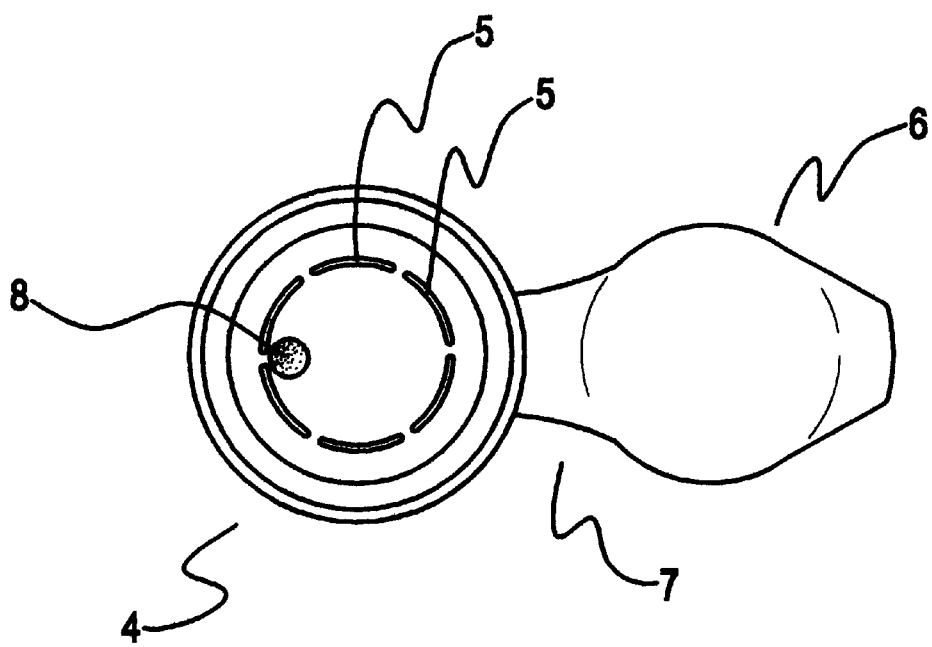
FIG. 5 is a bottom view of the cap in the open position.
Figure 6:
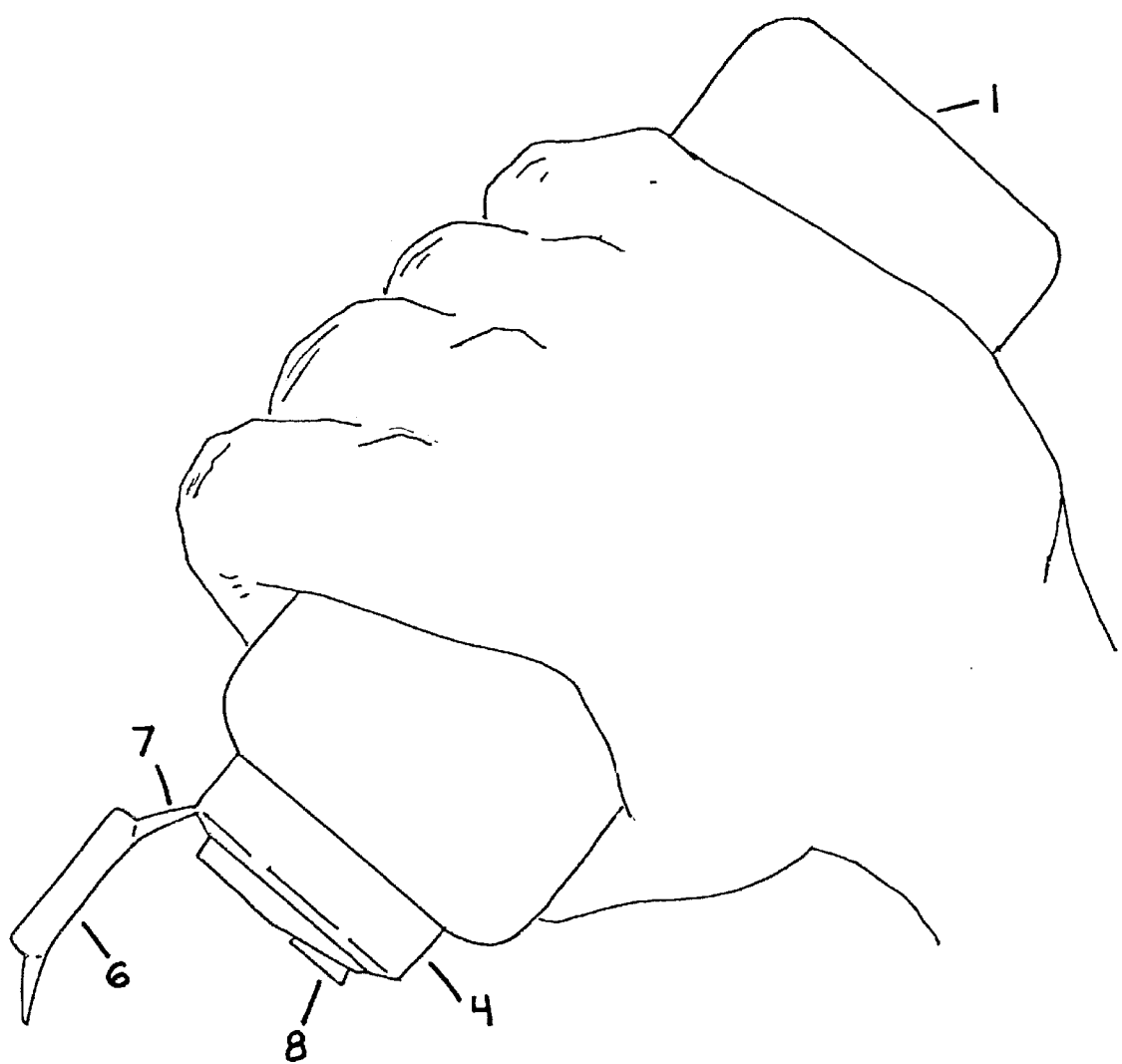
FIG. 6 is an illustration of the squeeze bottle in use.

Referring to FIGS. 1 and 2, the present invention further includes a squeeze bottle 1. The squeeze bottle 1 has a round mouth 2 and has raised threads 3 around the outside of the mouth 2, as shown on FIG. 2. Referring to FIGS. 3 through 5, a cap 4 is screwed onto the squeeze bottle 1 by engaging the groves 5 formed on the interior of cap 4 with the corresponding threads 3 on the mouth 2 of the squeeze bottle 1. The cap 4 further consists of a removable lid 6 which serves as a top for the cap 4 and is attached to the cap 4 by a plastic tether 7. The lid 6 fits over and seals the nozzle opening 8 in the cap 4. FIG. 6 shows how the squeeze bottle 1 is used with the lid 6 removed from the cap 4, so that the preferred mixture can be dispersed through the nozzle opening 8. Both the cap 4 and squeeze bottle 1 are made of plastic, although other materials that are non-reactive to acid could also be used.

In the preferred embodiment, the dry ingredients, namely the anhydrous citric acid and the activated carbon powder, are packaged in a 12-ounce, plastic, squeeze bottle. The necessary water can be added at a later time by the user. In this way, the squeeze bottle is very lightweight. Whenever the user prepares to go into the woods, the water can be added to the bottle by removing the cap, filling the bottle, and shaking the contents. The best way to ensure good mixing is to fill the bottle to half-full with water, close and shake the bottle, then fill the bottle to full and shake. The bottle should be vented after shaking to allow the release of gas pressure.

The tests performed using the preferred mixture show that it is highly effective in reducing the level of ammonia coming from urine treated with the mixture.

Tests 1 and 2—Untreated Urine

To measure the ambient ammonia level for a sample of human urine, a container of the urine was analyzed at normal room temperature. The exposed surface area for the urine was approximately 50 square inches.

In test 1, a Drager-Accuro bellows pump 2000 (Model 2000) was used to sample the air at a height of 6 inches above the surface of the urine. Specially calibrated tubes, identified as Drager CH20501 ammonia tubes, were used for sampling the air. These tubes have a measuring range of from 5 to 70 parts per million of ammonia. The results of the test showed that a level of 10 PPM of ammonia was generated by the sample of urine.

In test 2, a hand pump (having a squeeze bulb) was used with the Sensidyne Gastec Detector Tube No. 3L, which is designed to measure ammonia concentrations ranging from 0.5 to 78 PPM. The specific tubes for this test were marked as QC No. 70860. The results of the test showed a concentration of 8 PPM of ammonia in the air at 6 inches above the surface of the urine.

Tests 3 and 4—Urine Treated with Preferred Mixture

A sample of urine at room temperature was placed in the same container used in the previous tests. The sample was treated with the preferred mixture of the present invention.

In test 3, the same hand pump and calibrated tubes as employed in test 2 were used to sample the ammonia level in the air. The test results showed that the level of ammonia in the air at 6 inches above the treated solution was below the lower calibration range of 0.5 PPM.

In test 4, a SKC pocket pump (#8926789) was used to draw 24 liters of air through a treated silica gel tube placed 6 inches above the treated solution. The tube analysis was done by the Analytics Division of Laboratory Corporation of America® Holdings, using an analytical method identified as NIOSH 6016M. The results of the test showed that the concentration of ammonia was less than 0.15 PPM in the air sampled. Information concerning this analytical method and a copy of the test results are enclosed.

Overall reduction of ammonia level

Comparing the results from tests 2 and 4 shows a reduction of the ammonia level in the air from 8 PPM to less than 0.15 PPM. Therefore, applying the preferred mixture of the present invention reduced the ambient level of ammonia generated from the urine sample at the urine site by over 98%.

Field application trials

Four field trials were conducted during hunting season for white-tailed deer. The purpose of the trials was to see if deer approaching an area where the present invention had been used would show signs of awareness of foreign or unusual odors. Typical reactions of deer upon encountering unusual odors are: frequently stopping and raising their heads to better smell for scents as well as look and listen for movement, walking at a long distance around an area they would otherwise walk through directly, and jumping and running away from an area. Some wildlife experts speak of deer as having a "fright level", which goes up and down over time depending on how closely a deer associates an odor or sound with danger. These trials were conducted during hunting season when the deer's fright level would naturally be higher.

In each of the trials, the hunter urinated within several yards of a tree stand. The preferred mixture of the present invention was used in the following manner: a small depression in the ground was made (generally with the heel of a boot), about an ounce of the preferred mixture was poured into the depression, the hunter urinated into the depression, an additional two or more ounces of the preferred mixture were spread over the ground area wetted by the urine, and some dirt was scraped over the area.

In trial 1, two does and one buck approached approximately 25 minutes after applying the preferred mixture. They gave no indication that they noticed any unfamiliar scent or odor, even though they passed within 20 yards of the treated area. The hunter reported killing the buck. The weather conditions at the time were: 38° F., calm and cloudy.

In trial 2, two does approached approximately one hour after applying the preferred mixture. They passed within 20 yards of the treated area and continued walking through the woods. They showed no react ion to the treated area. The weather conditions at the time were: 44° F., calm and cloudy.

In trial 3, five deer approached approximately 30 minutes after applying the preferred mixture. They were directly downwind of the treated area. They continued walking toward the location of the hunter and the treated area. The hunter killed one buck. The weather conditions at the time were: 45° F., sunny and light wind.

In trial 4, one deer approached approximately 40 minutes after applying the preferred mixture. The deer was directly downwind of the hunter and the treated area. The deer continued walking toward the location of the treated area and passed within 18 yards of the hunter. The deer did not show any sign that she was aware of the treated area as she walked past. The weather conditions at the time were: 35° F., sunny and light wind.

The field trials have demonstrated that deer will come within close proximity of the location of the treated urine and that they do not react in a way that would indicate their awareness of foreign or unfamiliar scents and odors.

Factors associated with ammonia levels in the outdoors

The effectiveness of the present invention is augmented by several environmental factors. First, ammonia, at low levels, is a common odor in the outdoors. Animal urine contains ammonia, consequently any area inhabited by wildlife will have low levels of ammonia present in the air.

Thus, the presence of a very small amount of ammonia generated by urine treated with the present invention does not represent a strange or unusual odor to deer or other game animals.

Second, ammonia disperses well in the air because it has an atomic weight lower than nitrogen and oxygen, the two primary gases in our atmosphere, and because it has a low boiling point. This means that the low concentrations of ammonia emitted from urine treated with the present invention will not linger in an area. Third, air currents, such as convection and wind, operate to further disperse the ammonia.

Besides its effectiveness in reducing the odors produced by urine, some of the other major advantages of the present invention are that it is safe and easy to use, that it is compact and lightweight, and that it is economical because the ingredients are inexpensive.

The present invention makes it possible for a hunter to relieve himself in the outdoors without worrying that lingering odors from urine may alert wildlife of his presence. It allows a hunter, and others trying to get close to wildlife, to take fuller advantage of the outdoors because they can walk across a wide territory without leaving evidence of their presence.

What I claim is:

1. A method for eliminating odors from an area of ground wetted with human urine by:
   a. mixing anhydrous acid and activated carbon powder into a dry mixture;
   b. placing the dry mixture into a bottle having a removable lid for storage;
   c. adding water to the dry mixture inside the bottle to form an acidified, activated charcoal slurry; and
   d. dispensing the acidified, activated charcoal slurry onto the ground area that is wetted with urine to provide for complete treatment of the ammonia and other odor-producing chemicals present in the urine.

2. A method for treating odors generated from human urine during and after urination by:
   a. mixing an acid solution and activated carbon powder to form an acidified, activated charcoal slurry;
   b. storing the acidified, activated charcoal slurry in a bottle having a removable lid;
   c. dispensing one or more fluid ounces of the acidified, activated charcoal slurry onto the ground to prepare an area for urination by wetting the area with the acidified, activated charcoal slurry; and
   d. dispensing several ounces of the acidified, activated charcoal slurry on the same ground area after urination to allow for complete treatment of the ammonia and other odor-producing chemicals present in the urine.

3. An application unit for spreading a mixture onto an area of ground for the purpose of treating odors produced by urine, comprising:
   a. a squeeze bottle with an opening that is threaded;
   b. a mixture of anhydrous acid and activated carbon powder stored in the squeeze bottle for later mixing with water;
   c. a cap having corresponding threads that engage with the threads on the opening so that the cap seals the opening;
   d. a nozzle in the cap through which the contents of the squeeze bottle can be dispensed; and
   e. a means for opening and shutting the nozzle.

4. The application unit as described in claim 3, wherein water has been added to the mixture of anhydrous acid and activated carbon powder to form an acidified, activated charcoal slurry.

5. The application unit as described in claim 3, wherein the squeeze bottle, the cap and the nozzle are made of plastic or another material that is non-reactive to acid.

6. The application unit as described in claim 3, wherein the squeeze bottle has a volume capacity of between six and twenty fluid ounces.

7. The method as described in claim 1, wherein the bottle is a plastic, squeeze bottle having a volume capacity of between six and twenty fluid ounces.

8. The method as described in claim 1, wherein the anhydrous acid is a food grade, citric acid that has a pH level of approximately 2.2 when mixed with water in a ratio of one part anhydrous acid to 21 parts of water.

9. The method as described in claim 1, wherein the ratio of anhydrous acid to activated carbon powder is one part of anhydrous acid to two parts of activated carbon powder.

10. The method as described in claim 1, wherein the pH level of the acidified, activated charcoal slurry is 2.7, approximately.

11. The method as described in claim 2, wherein the bottle is a plastic, squeeze bottle having a volume capacity of between six and twenty fluid ounces.

12. The method as described in claim 2, wherein the acid solution has a pH level of 2.2, approximately.

13. The method as described in claim 2, wherein the acid solution is a food grade, citric acid having a pH level of 2.2, approximately.

14. The method as described in claim 2, wherein the ratio of the acid solution to the activated carbon powder is 11 parts of acid solution to one part of activated carbon powder.

15. The method as described in claim 2, wherein the pH level of the acidified, activated charcoal slurry is 2.7, approximately.

16. The application unit as described in claim 3, wherein the means for opening and shutting the nozzle is a lid that snaps over the nozzle.

17. The application unit as described in claim 3, wherein the means for opening and shutting the nozzle is a lid that snaps over the nozzle and has a tether that attaches the lid to the cap.

* * * * *